(12) United States Patent
Lethi

(10) Patent No.: US 6,394,093 B1
(45) Date of Patent: May 28, 2002

(54) NASOPHARYNGEAL AIRWAY WITH INFLATABLE CUFF

(76) Inventor: Scott Lethi, 319 Longstreet Dr., Greer, SC (US) 29650

( * ) Notice: Subject to any disclaimer, the term of this patent is extended or adjusted under 35 U.S.C. 154(b) by 0 days.

(21) Appl. No.: 09/311,463

(22) Filed: May 13, 1999

(51) Int. Cl.[7] .............. A61M 15/08; A62B 7/00
(52) U.S. Cl. .............. 128/207.18; 128/207.14; 128/207.13
(58) Field of Search .............. 128/200.26, 207.14, 128/207.15, 207.16, 207.17, 207.18

(56) References Cited

U.S. PATENT DOCUMENTS

| | | | | |
|---|---|---|---|---|
| 3,889,688 A | * | 6/1975 | Eamkaow | 128/207.15 |
| 3,915,173 A | * | 10/1975 | Brekke | 128/207.18 |
| 4,150,676 A | * | 4/1979 | Jackson | 128/207.15 |
| 4,231,365 A | * | 11/1980 | Scarberry | 128/207.15 |
| 4,240,417 A | * | 12/1980 | Holever | 128/203.12 |
| 4,256,099 A | * | 3/1981 | Dryden | 128/200.26 |
| 4,584,998 A | * | 4/1986 | McGrail | 128/207.14 |
| 4,593,689 A | * | 6/1986 | White | 128/201.19 |
| 4,751,924 A | * | 6/1988 | Hammerschmidt et al. | 128/207.15 |
| 4,791,923 A | * | 12/1988 | Shapiro | 128/207.14 |
| 4,819,619 A | * | 4/1989 | Augustine et al. | 128/200.26 |
| 4,821,715 A | | 4/1989 | Downing | 128/207.18 |
| 4,850,350 A | * | 7/1989 | Jackson | 128/207.16 |
| 4,898,168 A | * | 2/1990 | Yule | 128/207.15 |
| 5,285,777 A | * | 2/1994 | Beckwith | 128/207.15 |
| 5,303,697 A | * | 4/1994 | Brain | 128/200.26 |
| 5,499,625 A | * | 3/1996 | Frass et al. | 128/207.15 |
| 5,582,167 A | * | 12/1996 | Joseph | 128/207.15 |
| 5,664,567 A | | 9/1997 | Linder | 128/207.18 |
| 5,692,506 A | | 12/1997 | Linder | 128/642 |
| 5,791,341 A | * | 8/1998 | Bullard | 128/207.15 |
| 5,819,723 A | * | 10/1998 | Joseph | 128/207.14 |
| 5,819,733 A | * | 10/1998 | Bertram | 128/207.15 |

* cited by examiner

Primary Examiner—John G. Weiss
Assistant Examiner—Joseph F. Weiss

(57) ABSTRACT

An improved nasopharynx airway for draining fluids and supplying oxygen to a patient wherein the airway is locked into place by inflating a cuff which is provided around the distal end of the airway.

11 Claims, 2 Drawing Sheets

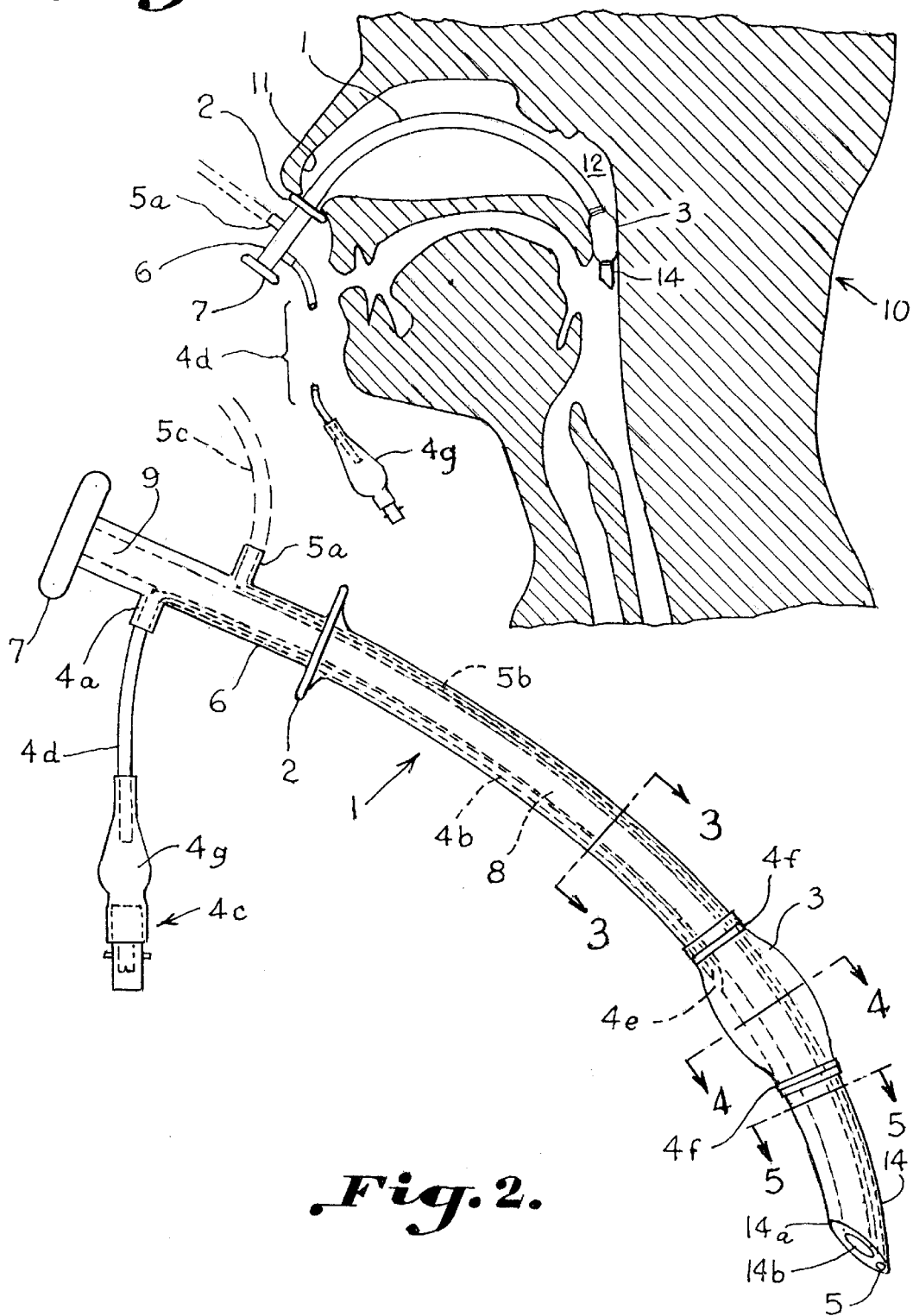

NASOPHARYNGEAL AIRWAY WITH INFLATABLE CUFF

FIELD OF THE INVENTION

This invention relates to improvements in nasopharyngeal airways which maintain the airway in a secure position so that oxygen may be reliably delivered to a patient and secretions may be removed without disturbing the position of the airway.

BACKGROUND OF THE INVENTION

Prior art nasopharyngeal airways usually consist of a tubular airway which can be inserted through a nostril of a patient with the purpose of creating a passageway to the throat to ensure that the patient has a consistently open breathing passage or airway. Depending on a patient's age, size, and anatomy, an effective airway may range from 4 inches to 6 inches long from the nares or nasal opening to the nasopharynx region. Semi-rigid, smooth, somewhat soft and pliable synthetic or natural rubber-like materials are generally used in constructing such airways. In a typically airway, a flange at the nasal end is used to hold the airway in place relative to the nasal passage.

Nasal airways find use during surgery or during other periods when it is vital that there will be an open breathing passage and the risk of collapse or obstruction must be obviated. Also, in periods of emergency or intensive care it is desirable that the airway be large enough to allow the introduction of a smaller tube through the airway for feeding, removing secretions, or treatments, or for insertion of a probe for observation.

Thus, it is a general object of the present invention to provide a nasal passageway which will remain in position when used in the foregoing described manner.

The continued and positive introduction and supply of oxygen to a patient is of utmost importance. In some prior art nasopharyngeal or transnasal airways an oxygen supply tube is run along the outside of the airway tube or through the interior of the tube. In both instances, the presence of an additional tube introduces unnecessary complications and also creates the risk that the additional tubing may be collapsed during other procedures performed through the airway. Accordingly, it is another object of the present invention to provide an airway which will protect the integrity of the oxygen supply to the patient.

One prior art nasopharyngeal airway is described in U.S. Pat. No. 4,821,715 which issued on Apr. 18, 1989 to Michael V. Downing. In the Downing patent an oxygen delivery lumen is provided within the wall of the airway tube but part of the lumen projects into the airway passageway and can be subject to being pinched or punctured or collapsed. Accordingly, it is still a further object of the present invention to provide an oxygen delivery lumen within a transnasal passageway which is protected from being collapsed or ruptured.

Also, in the above mentioned Downing airway there is no way to lock or secure the airway in place. When a probe or secretion removal nozzle is inserted, if there is any friction or rubbing or wedging, such probe or nozzle may also withdraw the airway as it is removed. Thus, it is a primary object of the present invention to provide a means and method for preventing the unwanted and premature withdrawal of an airway from a patient.

Other prior art transnasal passageways are shown and described in, for example, U.S. Pat. No. 5,664,567 which issued on Sep. 9, 1997 to Gerald S. Linder and in U.S. Pat. No. 5,692,506 which issued on Dec. 2, 1997 also to Gerald S. Linder. In the last mentioned patent, a transnasal passageway is shown which allows the introduction of a probe through the airway to monitor the results of certain surgical procedures. To hold the probe in place a thumb screw device is used. Still, when withdrawing the probe after release of the screw the possibility of either having to withdraw the airway completely and reinsert another is presented which adds to patient discomfort; and, also, to the likelihood that with each insertion and removal trauma can be introduced into surrounding nasal passage tissues. Thus, it is still another object of the present invention to provide a transnasal passageway which can be locked into place and remain for an extended period of time while providing oxygen and an open passageway for removal of secretions or introduction and removal of diagnostic probes.

The foregoing and other beneficial objects of the present invention will be apparent once the following Summary of the Invention, Drawings, and Detailed Descriptions are read and understood by those skilled in the art.

SUMMARY OF THE INVENTION

In one aspect the present invention is an improvement in nasopharyngeal or transnasal airways which comprises an inflatable cuff surrounding the airway adjacent the distal or interior end of the airway that can be inflated once it is inserted and positioned in the nasal passage of a patient so that the airway will be secured in place when the cuff is inflated.

In another aspect, the present invention is an improved nasopharyngeal airway for controlling drainage of naturally secreted fluids and for supplying oxygen to a patient who is either conscious or unconscious comprising a tube having sufficient rigidity so that lumens and ducts formed in its walls will not readily collapse, the tube having an open central passageway from end to end; a flange at one end of said tube, said flange being of sufficient diameter to prevent further insertion at the patient's nares; an inflatable cuff associated with the other or distal end of said tube; and, means for inflating the cuff when said tube has been inserted into the nasopharyngeal passageway of a patient up to said flange whereby when inflated said cuff and said flange operate to hold the tube securely in place. The tube may be provided with an extension which has ports for oxygen and for air. The oxygen port connects with a lumen that extends the length of the extension and the length of the tube and is formed integrally within the wall of the tube without creating a projection on the interior wall of the tube. The oxygen lumen terminates at the distal end of the tube in an orifice which is open to the patient's breathing passageways. The air port formed on the tube extension connects with an air duct which is preferably integrally formed in the tube extension and is coaxial with the wall of the tubing and is formed therein so that the duct does not form any projection into the central passageway of the airway. This duct continues to a point adjacent the distal end of the tube where it terminates in an orifice which opens on the outer surface of the tube. An inflatable membrane is attached over the opening at this point and is sealed to the outer surface of the tube around the opening. This membrane may be in the form of a sleeve made of hypo-allergenic rubber-like or thermoplastic materials. The requirements are that the membrane be flexible and air impervious and sealable to the tubing material. Such materials are well known to those skilled in the art. An air supply or syringe pump means is provided at the other or proximal end of the airway. The air supply means preferably comprises a syringe and one way valve that can inject just the small amount of air required to inflate the cuff, preferably about 3 cc to 8 cc.

In yet another aspect, the present invention is an improved method for providing continuous oxygenation and an open airway for a patient in a conscious or unconscious state comprising of the steps of providing a nasopharyngeal airway having an inflatable, locking cuff adjacent one end thereof, a nares contacting flange adjacent the other end of said airway; providing an oxygen supply lumen connecting to an opening at the locking cuff end of said airway, said lumen being coaxial with said airway to deliver oxygen at said opening; inserting said airway into a patient's nasal passageway to a position where said cuff is located in the posterior portion of the patient's nasopharynx; and, inflating said cuff to contact the wall of said nasopharynx to securely lock said airway so that subsequent patient movement, oxygenation or removal of secretions through said airway will not dislodge the position of said airway. For further understanding and appreciation of the invention and its advantages reference is made to the Drawings and Detailed Description below.

DESCRIPTION OF THE DRAWINGS

In the drawings which are appended hereto and made a part of this disclosure and which represent a preferred embodiment of the invention but are not limiting on the scope thereof:

FIG. 1 is a schematic representation of a section showing the nasopharyngeal cavity of a patient with the airway of the present invention placed therein;

FIG. 2 is a side elevation view of the airway of the present invention;

DETAILED DESCRIPTION OF THE INVENTION

Figure 3:
FIG. 3 is a cross-section along lines 3—3 of FIG. 2.

The best mode and preferred embodiment of my invention will now be described. Looking first at FIG. 1 which is an anatomical representation 10 of the nasal passageway or pharyngeal areas of a patient, nasopharyngeal tube or transnasal tube 1 is shown with flange 2 locked against nares 11. Flange 2 prevents further insertion of the tube and provides a firm anchor for the tube at the nares or proximal end of the tube. At the distal or other end of the tube or airway is inflatable cuff 3 in an inflated condition in the posterior nasopharynx region 12 with airway distal or inner tip 14 extending beyond the cuff. At the end of the tip, side 14a which is the "short" side of the tip should be on the outer side away from the direct contact with tissue so that the opening 14b faces down the throat.

In FIG. 2 the airway 1 of the present invention is shown in greater detail. The airway or tube 1 extends from flange 2 to the tip region 14 and is coaxial with a tube extension portion 6 which terminates at its upper or outer end in rim 7. The combined tube 1 and extension 9 have respective central passageways 6 and 8 which are aligned and which provide a continuous opening from rim 7 to the tip region 14 so that probes, secretion removal nozzles, and similar instruments and apparatus may be readily moved in and out. Adjacent the tip or distal end of the tube 1 inflated cuff 3 is positioned around the tube. When inflated as in the position shown in FIG. 1 the cuff locks the tube securely in place and works in conjunction with the flange 2 so that when probes or secretion removal instruments are passed through the passageways 6 and 8 the airway tube will not be dislodged.

Presently, prior art nasal tubes are sold in gauge sizes on a scale with size numbers running from No. 20 to No. 36 and the numbers are designated "French" numbers.

Still referring to FIG. 2, air port 4a and oxygen port 5b are shown formed into the extension 6. The air port 4a leads into duct 4b which extends from the port 4a and terminates in an opening in the outer wall of the tube at 4e. The duct 4b is formed integrally within the walls of tube 1 and extension 6 and its positioning can be appreciated by the cross-sections of the airway tube shown in FIGS. 3 and 4. It is preferred that the duct will be securely within the walls of the tube so the duct will not be collapsed or pinched due to insertion and removal of probes or other apparatus.

The means for inflating the cuff which is generally designated by the numeral 4 in FIG. 2 comprises valve 4c which is connected through line 4d to air port 4a. The inflation indicator 4 can be composed of a rubber-like material so that it will "balloon" outwardly and while it maintains inflation it indicates that pressure is up in the system and the cuff 3 is inflated.

A one way valve 4c is provided as is common in inflation retaining devices similar to those used in footballs and basketball. A syringe with a needle is preferably used as the inflation means to inject air through valve 4c. Air for inflation travels along the duct 4b and enters the cuff 3 through opening 4e which can be seen in greater detail in FIG. 4 which is a section along line 4—4 of FIG. 2. The cross-section of the cuff 3 is shown here with a plurality of peaks ribs 13 with valleys therebetween. This is a representation of the cuff before it is fully inflated and is partially collapsed as shown. Effective contact with the surrounding tissue is provided as the cuff is inflated. Drainage of any nasal tissue secretions into the throat and lungs is prevented when the cuff is inflated around the airway tube. It is within the scope of the invention to provide a number of configurations for the surface of the cuff. Specifically, the cuff can have a completely smooth surface or the cuff may have a ribbed surface, either longitudinally or transversely. A ribbed or pleated surface allows greater expansive surface and volume for the cuff. Furthermore, the cuff may only be located on one side of the tube. The cuff 3 may be made of any soft, flexible, air impervious material such as a thermoplastic sheet-like material. In construction, a sleeve may be positioned over the opening 4e and heat sealed around the tube with seals 4f. The distance from cuff to tip is typically about 3.0 cm. While it is preferred that a pneumatic system be used as a cuff inflating or expansion means, it is also within the scope of the invention to use a hydraulic or fluid means to inflate or expand the cuff 3.

Figure 5:
FIG. 5 is a section along lines 5—5 of FIG. 2.
Figure 4:
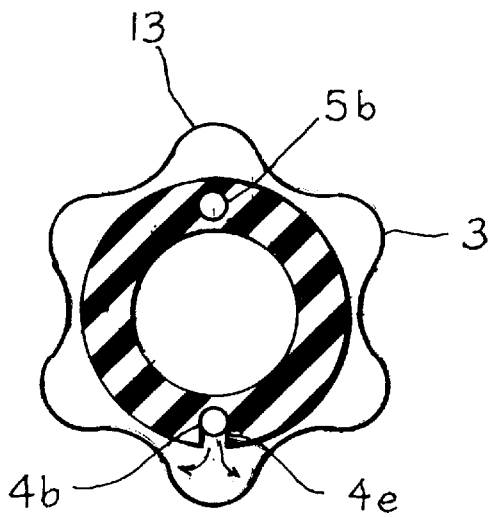
FIG. 4 is a cross-section through lines 4—4 of FIG. 2.

Also in FIG. 2 the means for delivering a supply of oxygen 5 can be seen. This means includes the oxygen port 5a, the supply line 5c which is connected to the hospital room oxygen supply system or to a portable oxygen tank which is connected through the port 5a to lumen 5b which extends to the tip of the tube 14 and terminates in opening 5. The continuous extension of lumen 5b is shown in FIGS. 3, 4, and 5 which show the respective sections from tube 1 from FIG. 2. Again, it is a desirable feature that the oxygen supply lumen be formed integrally within the wall of the tube so that it is protected against collapse and pinching. It is also important that it has a distinct opening as shown at the tip in FIG. 2 so that a supply of oxygen is always available to the patient as well as having an open access canal for treatments.

In operation, a variety of airway tube diameters and lengths would be available for the differences in the physical dimensions of various patients. Typically, the airway of the present invention would be used for short term patients and would be deflated every four to six hours and checked to see if inflation is being maintained. In operation, once the proper length and size is selected and the airway inserted into the patient's nostril up to the nares where the flange is in contact with the nares, the air is introduced by the syringe so that the internal pressure of the cuff would run between 6 psi to 15 psi and no greater than 20 psi which is achieved with 3 cc to 8 cc of air. An air pressure gauge may be included in the inflating means so that the pressure can be readily monitored.

The airway of the present invention is especially useful where there has been surgery and post-operative progress is to be observed, or there is an infection of the lungs and/or it is necessary to withdraw secretions therefrom. Also, with facial trauma, stroke victims, senior, or unconscious patients or for patients with a weak coughing reflex the airway of the present invention provides a positive removal channel. The cuff preferably is located at the distal portion of the nasal pharynx area and above the epiglottis, that is, the superior part of the throat. As previously mentioned, the cuff provides an additional advantage in that it can block unwanted secretions from the nasal area from draining into the throat and lungs.

While the above description sets forth a preferred embodiment of the airway of the present invention, it is to be understood that the invention is not limited thereby and that in light of the present disclosure of the invention other alternative embodiments will be apparent to those skilled in the art. Accordingly, it is to be understood that changes may be made without departing from the scope of the invention as particularly set out and claimed below.

What is claimed is:

1. An improved nasopharyngeal airway for drainage of fluids and supply of oxygen to a patient comprising:
    a) an airway tube having a cylindrical wall with proximal and distal ends, said proximal end arranged to be positioned externally of the patient at the patient's nares and said distal end arranged to be inserted into a nasal passage of a patient and positioned in the internal end said nasal passage, said tube having sufficient rigidity so that lumens and ducts formed in its walls will not readily collapse, said tube having an open central passageway from said proximal end to said distal end;
    b) a flange at the proximal end of said tube, said sufficient diameter to prevent further insertion of said tube at the nares;
    c) a tube extension extending outwardly from said flange at said proximal end and having an open central passageway which acts to extend the central passageway of said airway tube, said tube extension terminating in a rim;
    d) an inflatable cuff associated with the distal end of said tube positioned and adapted to engage the patient's nasopharynx when in use;
    e) means for inflating said cuff when said tube has been inserted into a nasopharyngeal passageway of a patient whereby the inflated cuff will hold said airway tube securely in place within the nasopharynx of the patient;
    f) a lumen formed within the wall of said tube and extending the length thereof; and,
    g) means providing for the delivery of a supply of oxygen to the distal end of said tube through said lumen said lumen having an opening in the surface of the distal end of said tube whereby when fluids are removed through said central passageway, air or oxygen may be supplied through said lumen to the patient.

2. The improved airway of claim 1 wherein said means providing for the delivery of a supply of oxygen comprises:
    a) a supply line for delivering oxygen from an oxygen source; and,
    b) an oxygen port located on said tube extension adapted for connection with said oxygen supply line.

3. The improved airway of claim 1 wherein the means for inflating said cuff comprises:
    a) an air supply port in said extension for receiving an air supply line;
    b) an air supply duct located in said tube wall and connecting said air port and said cuff;
    c) air supply means and valve for supplying air through said port and duct to said cuff; and,
    d) an inflation indicator for indicating the inflation pressure in the cuff.

4. The improved airway of claim 1 wherein said cuff extends around the outer surface of the tube adjacent the distal end of said tube for a portion of the length of said tube.

5. The improved airway of claim 4 wherein the surface of said cuff is continuous and smooth.

6. The improved airway of claim 4 wherein said cuff is ribbed.

7. The improved airway of claim 4 wherein said tube is formed from a hypo-allergenic, flexible material.

8. An operably positioned nasopharyngeal airway comprising:
    a) a human patient having a nasal passageway in which said airway is positioned, said airway further comprising:
    b) a tube having spaced apart distal and proximal ends and a wall, said wall having sufficient rigidity to prevent the collapse of ducts and lumens formed in the tube wall, said tube having an open central passageway from end to end;
    c) a flange integrally formed with the tube, said flange being positioned at one end of the tube which is the proximal end thereof to prevent further insertion of the tube into the nasal passageway of the patient;
    d) an inflatable cuff disposed around the outer surface of the tube and being located adjacent the distal end of said tube, said cuff being adapted to engage the patient's nasopharynx, the distance between said flange and said cuff being pre-selected to approximate the distance from the nares to the posterior nasopharynx of the patient;
    e) a tube extension coaxial with and integrally formed with said tube, said extension being integral with said flange at one end and terminating in a rim at its other end, said extension having an air and an oxygen port formed therein;
    f) means providing for inflation of said cuff, said means comprising a duct extending from said cuff to said air port, a connection for a syringe and one way valve, and a supply line connecting said syringe and said port; and,
    g) oxygen supply means comprising an orifice in the tip of said tube adjacent said cuff, a lumen extending from said opening to said oxygen port, said port being connectable to a supply of oxygen, whereby said improved airway is inserted in the nasopharyngeal passage of the patient up to said flange, the cuff upon inflation will contact the nasal passage walls of the patient providing a secure passageway so that oxygen may be introduced through said lumen and secretions may be withdrawn through the open tube passageway.

9. An improved method of providing continuous oxygenation and an open airway while allowing removal of secretions from a patient in a conscious or unconscious state comprising the steps of:

a) providing a nasopharyngeal airway having distal and proximal ends and having an inflatable nasopharynx locking cuff adjacent the distal end thereof and a nares contacting flange adjacent the proximal end, said airway having an air duct coextensive therewith;

b) providing an oxygen supply lumen connected to an opening at the locking cuff end of said airway, said lumen being coaxial with said airway to deliver oxygen at said opening;

c) inserting said airway into a patient's nasal passageway to a position where said cuff is located in the posterior portion of the patient's nasopharynx is positioned adjacent the nares of the patient; and, d) inflating said cuff to contact the walls of said nasopharynx to securely lock said airway so that subsequent patient movement, oxygenation, or removal of secretions through said airway can occur and not dislodge the position of said airway.

10. The improved method of claim 9 wherein said air duct terminates in an orifice on the surface of the tube adjacent said one end of said tube and said cuff comprises an air impervious membrane hermetically sealed to the outer surface of the tube around said orifice whereby when air is introduced through said orifice the membrane inflates and expands to a secured position in contact with the surface of the patient's nasal passageway.

11. The improved method of claim 10 wherein said membrane is sealed completely around the circumference of said airway tube by two longitudinally spaced apart seals to form a sleeve-like cuff.

* * * * *